(12) United States Patent
Hsieh et al.

(10) Patent No.: US 11,004,709 B2
(45) Date of Patent: May 11, 2021

(54) METHOD FOR MONITORING GAS IN WAFER PROCESSING SYSTEM

(71) Applicant: Taiwan Semiconductor Manufacturing Co., Ltd., Hsinchu (TW)

(72) Inventors: Wen-Chieh Hsieh, Tainan (TW); Su-Yu Yeh, Tainan (TW); Ko-Bin Kao, Taichung (TW); Chia-Hung Chung, Shanhua Township, Tainan County (TW); Li-Jen Wu, Tainan (TW); Chun-Yu Chen, Tainan (TW); Hung-Ming Chen, Kaohsiung (TW); Yong-Ting Wu, Tainan (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 16/127,919

(22) Filed: Sep. 11, 2018

(65) Prior Publication Data
US 2019/0157124 A1 May 23, 2019

Related U.S. Application Data

(60) Provisional application No. 62/588,486, filed on Nov. 20, 2017.

(51) Int. Cl.
*H01L 21/67* (2006.01)
*G01N 33/00* (2006.01)
*H01L 21/673* (2006.01)
*B05C 15/00* (2006.01)

(52) U.S. Cl.
CPC ........ *H01L 21/67253* (2013.01); *B05C 15/00* (2013.01); *G01N 33/0065* (2013.01); *H01L 21/67017* (2013.01); *H01L 21/6719* (2013.01); *H01L 21/67393* (2013.01); *H01L 21/67011* (2013.01)

(58) Field of Classification Search
None
See application file for complete search history.

(56) References Cited

U.S. PATENT DOCUMENTS

2008/0264338 A1* 10/2008 Otsuki ................ C23C 16/4405
118/712
2015/0129044 A1* 5/2015 Chou ................ H01L 21/67253
137/14

* cited by examiner

*Primary Examiner* — Jethro M. Pence
(74) *Attorney, Agent, or Firm* — McClure, Qualey & Rodack, LLP

(57) ABSTRACT

A method for monitoring gas in a wafer processing system is provided. The method includes producing an exhaust flow in an exhausting conduit from a processing chamber. The method further includes placing a gas sensor in fluid communication with a detection point located in the exhausting conduit via a sampling tube that passes through a through hole formed on the exhausting conduit. The detection point is located away from the through hole. The method also includes detecting a gas condition at the detection point with the gas sensor. In addition, the method also includes analyzing the gas condition detected by the gas sensor to determine if the gas condition in the exhausting conduit is in a range of values.

20 Claims, 7 Drawing Sheets

METHOD FOR MONITORING GAS IN WAFER PROCESSING SYSTEM

PRIORITY CLAIM AND CROSS-REFERENCE

This application claims the benefit of U.S. Provisional Application No. 62/588,486, filed on Nov. 20, 2017, the entirety of which is incorporated by reference herein.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometric size (i.e., the smallest component (or line) that can be created using a fabrication process) has decreased. This scaling-down process generally provides benefits by increasing production efficiency and lowering associated costs. Such scaling-down has also increased the complexity of processing and manufacturing ICs.

ICs are typically fabricated by processing one or more wafers as a "lot" with a series of wafer fabrication tools (i.e., "processing tools"). Each processing tool typically performs a single wafer fabrication task on the wafers in a given lot. For example, a particular processing tool may perform layering, patterning and doping operations or thermal treatment. A layering operation typically adds a layer of a desired material to an exposed wafer surface. A patterning operation typically removes selected portions of one or more layers formed by layering. A doping operation typically incorporates dopants directly into the silicon through the wafer surface, to produce p-n junctions. A thermal treatment typically heats a wafer to achieve specific results (e.g., dopant drive-in or annealing).

Although existing methods and devices for operating the processing tool have been generally adequate for their intended purposes, they have not been entirely satisfactory in all respects. Consequently, it would be desirable to provide a solution for the process control for semiconductor manufacturing operations.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

Figure 1:
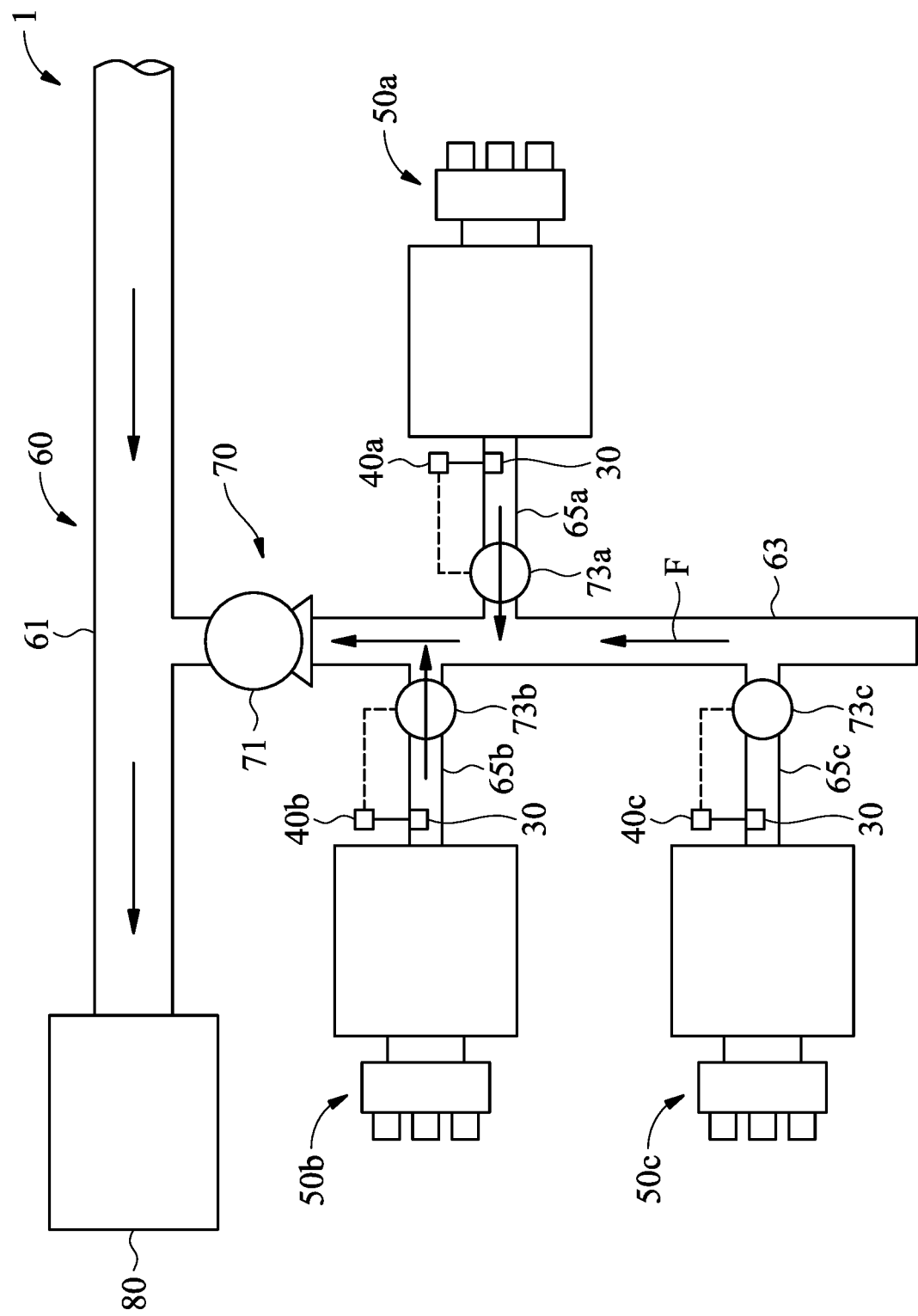
FIG. 1 shows a schematic view of a wafer processing system, in accordance with some embodiments.

The following disclosure provides many different embodiments, or examples, for implementing different features of the subject matter provided. Specific examples of solutions and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. It should be understood that additional operations can be provided before, during, and after the method, and some of the operations described can be replaced or eliminated for other embodiments of the method.

Referring to FIG. 1, a schematic view of a wafer processing system 1 is illustrated, in accordance with some embodiments. In some embodiments, the wafer processing system 1 includes one or more processing apparatuses, such as wafer processing apparatuses 50a, 50b, and 50c, a fluid conduit assembly 60, a flow-control assembly 70 and a gas handling apparatus 80. It is appreciated that the number of wafer processing apparatuses 50a, 50b, and 50c can be varied according to different manufacturing procedures.

The wafer processing apparatuses 50a, 50b, and 50c are configured to perform manufacturing procedures involved in the processing of one or more wafers. The wafer processed by the wafer processing apparatuses 50a, 50b, and 50c may include a semiconductor, conductor, and/or insulator layers. In some embodiments, the wafer includes layered semiconductors. Examples include the layering of a semiconductor layer on an insulator such as that used to produce a siliconon-insulator (SOI) wafer, a silicon-on-sapphire wafer, or a silicon-germanium-on-insulator wafer, or the layering of a semiconductor on glass to produce a thin film transistor (TFT). The wafer may go through many processing steps, such as lithography, etching, and/or doping before a completed die is formed.

Figure 2:
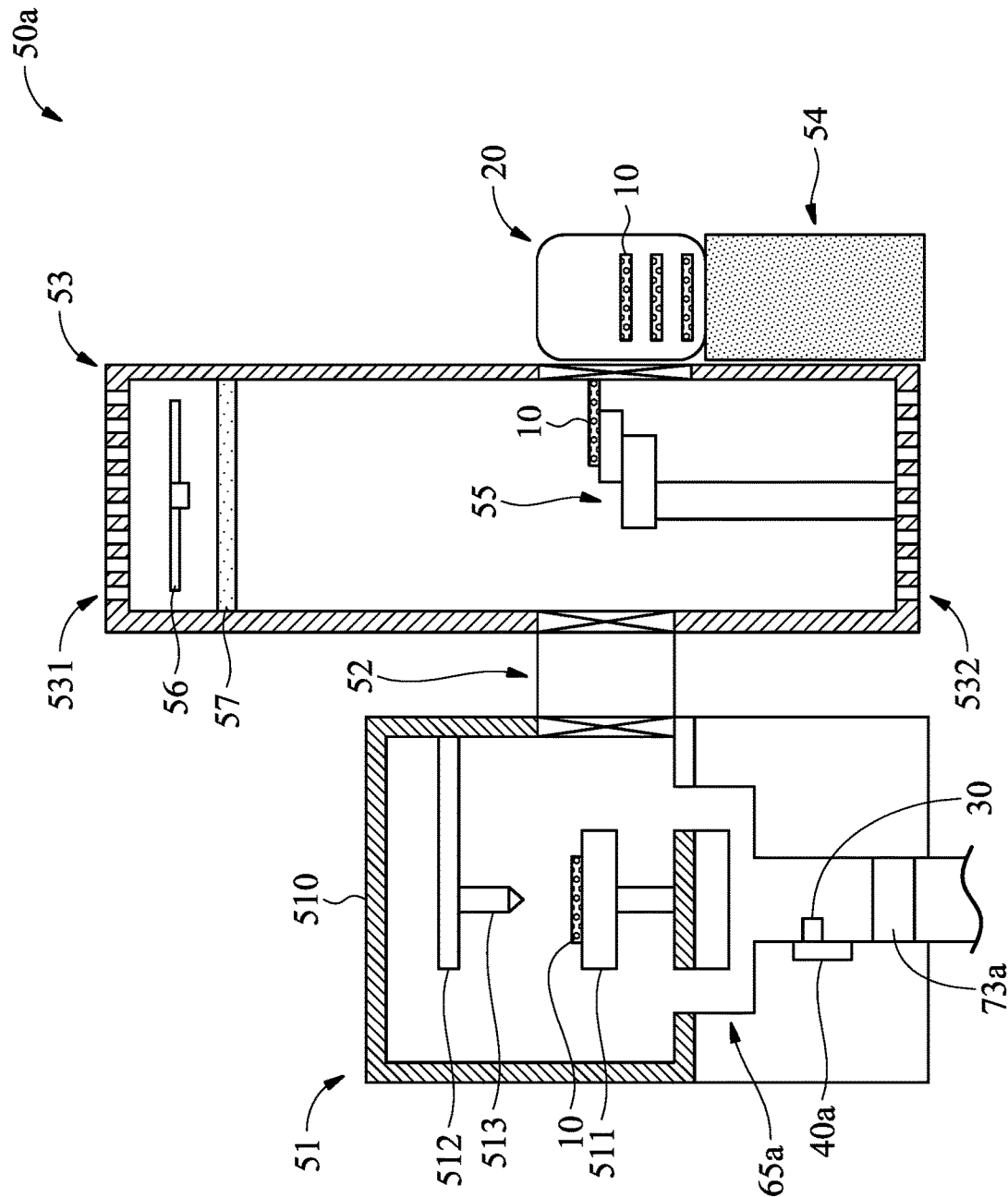
FIG. 2 shows a schematic view of a wafer processing apparatus with an exhaust conduit connected to a processing chamber thereof, in accordance with some embodiments.

According to the different manufacturing procedures that the wafer processing apparatuses 50a, 50b, and 50c performs, the wafer processing apparatuses 50a, 50b, and 50c can include different features. For example, as shown in FIG. 2, the wafer processing apparatus 50a includes a processing module 51, a load lock module 52, an interface module 53, one or more load port 54, and one or more wafer transfer module 55, in accordance with some embodiments. It is appreciated that the features described below can be replaced or eliminated in other embodiments of the wafer processing apparatus 50a.

In some embodiments, the processing module 51 is configured to perform a photoresist dispensing process. In such embodiments, the process module 51 includes a processing chamber 510, a wafer stage 511, a robotic arm 512 and a dispensing nozzle 513. The wafer stage 511 is configured for holding, positioning, moving, and otherwise manipulating the wafer 10. The wafer 10 may be secured on the wafer stage 511 by a clamping mechanism, such as vacuum clamping or e-chuck clamping. In addition, the wafer stage 511 may be designed and configured to be operable for translational and rotational motions. The dispensing nozzle 513 is mounted on the robotic arm 512 and connected to a source unit (not shown in figures) to receive the chemical solution from the source unit. The robotic arm 512 is configured to drive both radial and rotational movement of the dispensing nozzle 513 that is used to apply a chemical solution, such as photoresist, to the wafer 10.

However, it should be appreciated that many variations and modifications can be made to embodiments of the disclosure. The processing module 51 may be configured to perform any manufacturing procedure on a wafer 10. In some other embodiments, the processing module 51 is configured to perform manufacturing procedures that include deposition processes such as physical vapor deposition (PVD), chemical vapor deposition (CVD), plasma-enhanced chemical vapor deposition (PECVD) and/or other deposition processes.

In yet other embodiments, the processing module 51 is configured to perform manufacturing procedures that include etching processes such as wet etching, dry etching or ion beam milling. In still yet other embodiments, the processing module 51 is configured to perform manufacturing procedures including lithographic exposure, ion implantation, thermal processes, cleaning processes, testing, any procedure involved in the processing of the wafer 10, and/or any combination of such procedures.

The load lock module 52 is arranged between the processing module 51 and the interface module 53. The load lock module 52 is configured for preserving the atmosphere within the processing module 51 by separating it from the interface module 53. When the wafer 10 is inserted into the load lock module 52, the load lock module 52 is sealed. The load lock module 52 is capable of creating an atmosphere compatible with the processing module 51 or the interface module 53 depending on where the loaded wafer 10 is scheduled to be next. This can be performed by altering the gas content of the load lock module 52 by such mechanisms as adding gas or creating a vacuum, along with other suitable means for adjusting the atmosphere in the load lock module 52. When the correct atmosphere has been reached, the wafer 10 can be accessed.

In some embodiments, the interface module 53 is a facility interface. In some embodiments, the interface module 53 includes an equipment front end module (EFEM). The interface module 53 may include a fan assembly 56 and a filter assembly 57 positioned at the top 531. The fan assembly 56 is configured to actuate a gas flow into the interface module 53 via orifices formed on the top 531, and to exhaust the gas flow out of the interface module 53 via orifices formed on the bottom 532. The filter assembly 57 removes particles in the gas flow.

In some embodiments, the load port 54 is adjacent to the interface module 53. In some embodiments, an overhead hoist transport (OHT) (not shown in figures) transports a carrier 20, such as a standard mechanical interface (SMIF) or a front opening unified pod (FOUP) with the wafer 10 from a stocker (not shown in figures) to the load port 54. When the carrier 20 is located on the load port 54, the wafer 10 in the carrier 20 is transferred to the interface module 53 by the wafer transfer module 55.

Referring again to FIG. 1, the fluid conduit assembly 60 includes a main conduit 61, a domain conduit 63, one or more exhausting conduits, such as exhausting conduits 65a, 65b, and 65c, in accordance with some embodiments.

The main conduit 61 is fluidly connected between the gas handling apparatus 80 and the domain conduit 63. The main conduit 61 allows the gas to flow from the domain conduit 63 to the gas handling apparatus 80. According to manufacturing requirements, the gas handling apparatus 80 may contain filtering capacity as well as air movement capabilities. For example, the gas handling apparatus 80 includes a fan, a filter assembly to clean gas, and a gas cooling assembly to cool gas.

In some other embodiments, the wafer processing system 1 includes a number of domain conduits 63 (only one domain conduit 63 is shown in FIG. 1). The domain conduits 63 are fluidly connected to the main conduit 61, and the flow of gas from each domain conduit 63 is moved to the gas handling apparatus 80 via the main conduit 61. The main conduit 61 and the domain conduits 63 may be located below a manufacturing floor at which the wafer processing apparatuses 50a, 50b, and 50c are positioned.

The exhausting conduits 65a, 65b, and 65c are respectively fluidly connected between the domain conduit 63 and the wafer processing apparatuses 50a, 50b, and 50c. The exhausting conduits 65a, 65b, and 65c are physically connected to a vacuum environment of the wafer processing apparatuses 50a, 50b, and 50c. For example, as shown in FIG. 2, the exhausting conduit 65a is connected to a bottom wall of the processing chamber 510 of the wafer processing apparatus 50a.

The number of exhausting conduits can be varied according to demand. In some embodiments, the number of exhausting conduits corresponds to the number of processing apparatuses. In some other embodiments, the number of exhausting conduits is greater or less than the number of wafer processing apparatuses. Some of the wafer processing apparatuses may connect to one or more exhausting conduits, and some of the wafer processing apparatuses may not connect to an exhausting conduit.

The flow-control assembly 70 includes a flow actuating member 71, and one or more flow-control members, such as flow-control members 73a, 73b, and 73c, in accordance with some embodiments. The flow actuating member 71 is positioned in the domain conduit 63 and configured to produce an exhaust flow F in the domain conduit 63 and the exhausting conduits 65*a*, 65*b*, and 65*c*, as indicated by the arrows in FIG. 1. As a result, the gas in the wafer processing apparatuses 50*a*, 50*b*, and 50*c* is exhausted to the gas handling apparatus 80 via the exhausting conduits 65*a*, 65*b*, and 65*c*, the domain conduit 63 and the main conduit 61. The flow actuating member 71 may include, for example, a fan, a blower or a pump.

The flow-control members 73*a*, 73*b*, and 73*c* are configured to control the amount of the exhaust flow from the corresponding wafer processing apparatuses 50*a*, 50*b*, and 50*c*. In some embodiments, the flow-control members 73*a*, 73*b*, and 73*c* are respectively mounted in the exhausting conduits 65*a*, 65*b*, and 65*c*. The flow-control members 73*a*, 73*b*, and 73*c* may include throttle valve, mass flow controller (MFC), electric proportional valve or solenoid proportional valve.

The wafer processing system 1 further includes gas sensors 40*a*, 40*b* and 40*c* configured to detect the gas condition in the exhausting conduits 65*a*, 65*b*, and 65*c*, respectively, and send data associated with the gas condition in the exhausting conduits 65*a*, 65*b*, and 65*c*, respectively, to the flow-control members 73*a*, 73*b*, and 73*c* for performing a closed-loop flow-control. In some embodiments, the gas sensors 40*a*, 40*b* and 40*c* are respectively mounted in the exhausting conduits 65*a*, 65*b*, and 65*c*. The gas sensors 40*a*, 40*b* and 40*c* may be located at an upstream side of the corresponding flow-control members 73*a*, 73*b*, and 73*c*.

In some embodiments, as shown in FIG. 1, the gas sensors 40*a*, 40*b* and 40*c* are positioned outside of the exhausting conduits 65*a*, 65*b*, and 65*c*, and the gas in the exhausting conduits 65*a*, 65*b*, and 65*c* is collected by gas collecting structures 30 which are directly connected to the exhausting conduits 65*a*, 65*b*, and 65*c*. The gas sensors 40*a*, 40*b* and 40*c* may include detecting meters to detect the exhaust pressure of the gas flow, the temperature of the gas flow, the concentration of contamination particles of the exhaust flow, etc.

The structural features of one of the gas collecting structures 30 are described below, in accordance with some embodiments.

Figure 3:
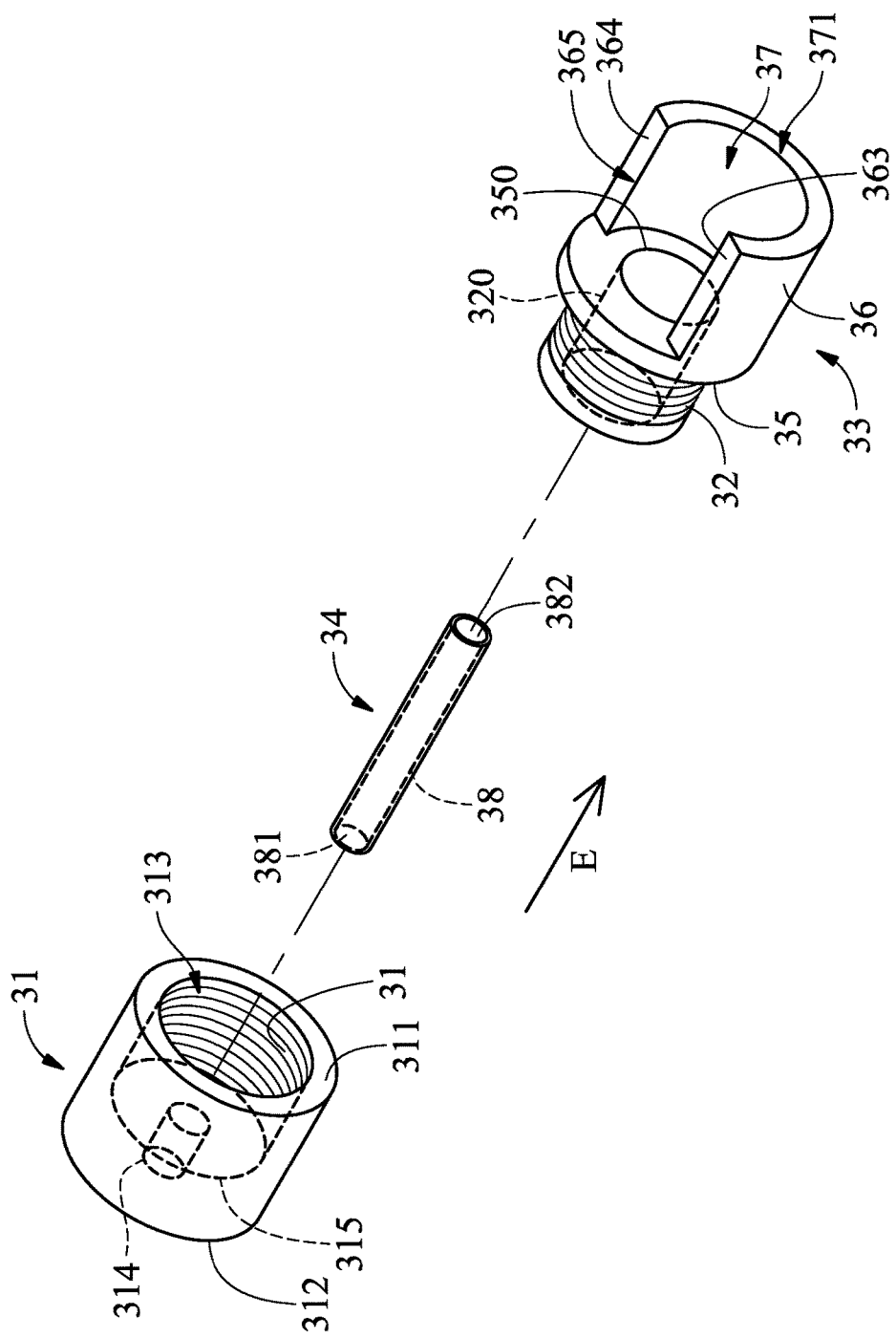
FIG. 3 shows an exploded view of a gas collecting structure, in accordance with some embodiments.

FIG. 3 shows a schematic view of a gas collecting structure 30, in accordance with some embodiments. In some embodiments, the gas collecting structure 30 includes a fastening seat 31, an engaging member 32, a shelter member 33 and a sampling tube 34.

In some embodiments, the fastening seat 31 includes a cylinder block with a front surface 311 and a rear surface 312 on its two opposite sides. A recess 313 is formed on the front surface 311 of the fastening seat 31. In addition, a bore 314 is formed on the rear surface 312 of the fastening seat 31. The bore 314 connects the rear surface 312 to a bottom surface 315 of the recess 313. As a result, the bore 314 is communicated with the recess 313.

Figure 6:
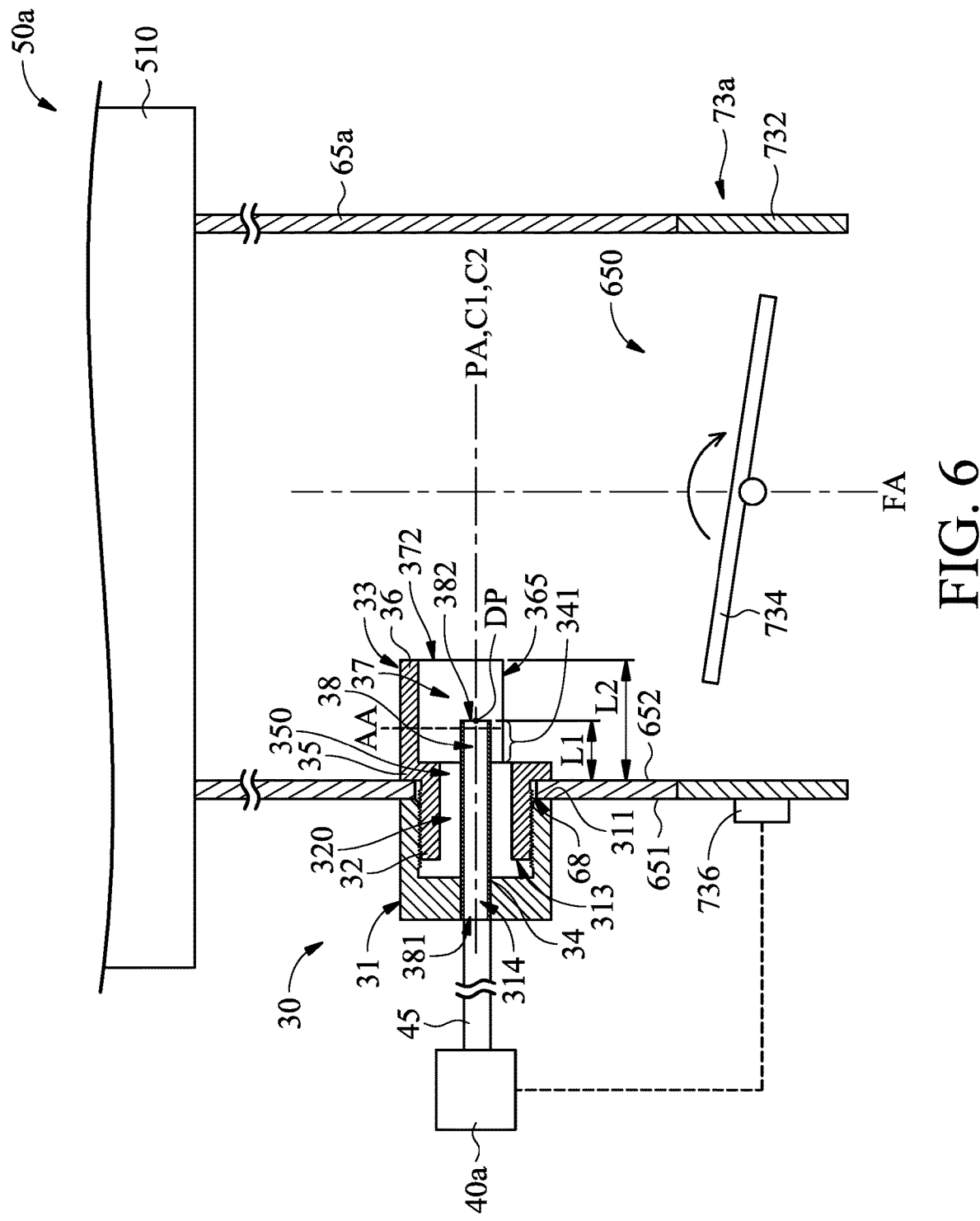
FIG. 6 shows a cross-sectional view of a gas collecting structure as mounting on an exhausting conduit that connects a processing chamber and a flow-control member with a shelter member positioned at an upstream side of a sampling tube, in accordance with some embodiments.

The engaging member 32 is configured to affix the shelter member 33 to the fastening seat 31. The engaging member 32 may have a shape that is compatible with the recess 313 of the fastening seat 31, and an external thread may be formed on an outer surface of the engaging member 32 for engagement with an internal thread formed on an inner wall of the recess 313. In addition, a passage 320 is formed in the engaging member 32 (FIG. 6 shows this feature more clearly.) The passage 320 has a width that is sufficiently greater than the width of the sampling tube 34 so as to allow the sampling tube 34 to pass through.

The shelter member 33 is configured to prevent the sampling tube 34 from being contaminated by particles in the exhaust flow in the exhausting conduit 65*a* (FIG. 2). In some embodiments, the shelter member 33 includes a connecting portion 35 and an extension portion 36. The extension portion 36 is integrally connected to the engaging member 32 via the connecting portion 35. The connecting portion 35 has a plate-shaped body with a passage 350 formed relative to the passage 320. (FIG. 6 shows this feature more clearly). The passage 350 may have the same width as that of the passage 320.

Figure 4:
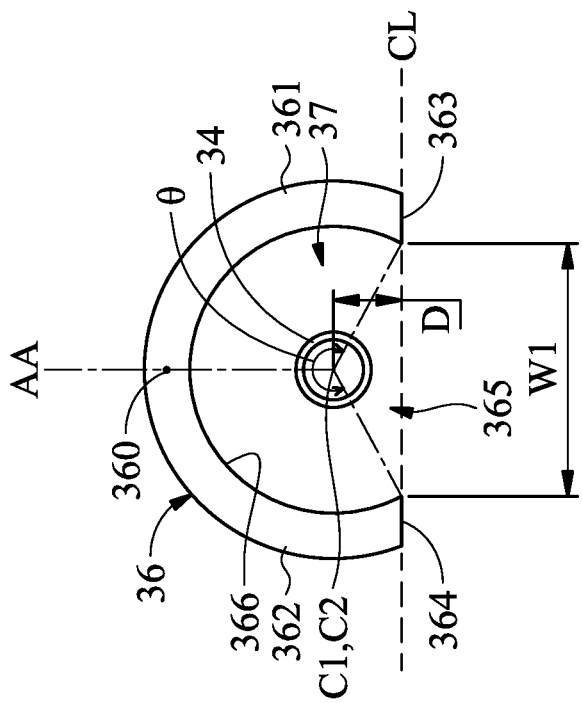
FIG. 4 shows a cross-sectional view of a gas collecting structure with an arc-shaped shelter member positioned above a sampling tube, in accordance with some embodiments.

The extension portion 36 protrudes from an outer edge of the connecting portion 35 along the extension direction E. In some embodiments, as shown in FIG. 4, a cross section of the extension portion 36 has an arc-shape with two leg sections 361 and 362 connected with each other at an apex node 360. The two leg sections 361 and 362 extend from the apex node 360 and terminate at two lower edges 363 and 364, respectively. The arc angle θ of the extension portion 36 is greater than 180 degrees.

Additionally, the extension portion 36 has an outer channel 37 formed therein. The outer channel 37 may have a sector-shaped cross-section. The boundary of sector-shaped cross-section is located on an inner surface 366 of the extension portion 36 and a connecting line CL of the two lower edges 363 and 364. As shown in FIG. 3, the outer channel 37 has an opening 371 formed on one side of the extension portion 36 that is opposite to the connecting portion 35. A long cut 365 is formed between the two lower edges 363 and 364 and communicates with the outer channel 37. The long cut 365 extends along the extension direction E and connects to the opening 371. The width W1 of the long cut 365 may be greater than an outer diameter of the sampling tube 34.

It should be appreciated that the shape of the extension portion 36 should not be limited to the embodiments shown above. The shape can be modified as long as a turbulence of the gas flow passing through the extension portion 36 is not incurred. For example, in the embodiment shown in FIG. 5, the extension portion 36' has a triangular cross-section with two leg sections 361' and 362' connected with each other at an apex node 360'. The two leg sections 361' and 362' extend downwardly and outwardly from the apex node 360' and terminate at two lower edge 363' and 364', respectively.

Figure 5:
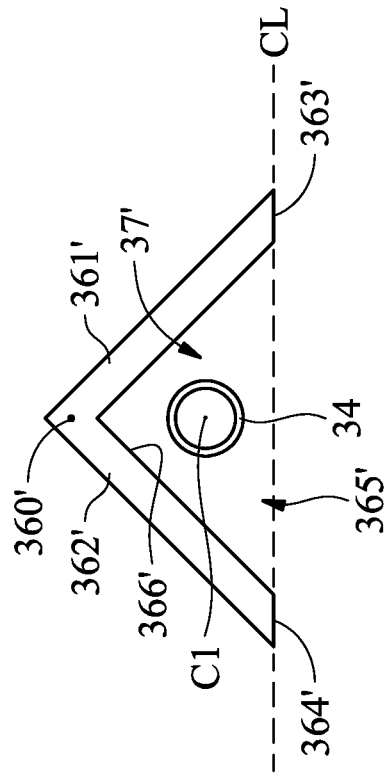
FIG. 5 shows a cross-sectional view of a gas collecting structure with a rectangular shelter member positioned above a sampling tube, in accordance with some embodiments.

In the embodiment shown in FIG. 5, the extension portion 36' has an outer channel 37'. The boundary of outer channel 37' is located on an inner surface 366' of the extension portion 36' and a connecting line CL that is connected between the two lower edges 363' and 364'. The outer channel 37' may have a triangular cross-section. In addition, the extension portion 36' has a long cut 365' formed between the two lower edges 363' and 364' and communicates with the outer channel 37'.

Referring back to FIG. 3 again, in some embodiments, the sampling tube 34 extends along the extension direction E with a length that is sufficiently greater than a depth of the recess 313 of the fastening seat 31. An inner channel 38 penetrates the sampling tube 34 with two openings 381 and 382 formed on two ends of the sampling tube 34 in the extension direction E (FIG. 6 shows this feature more clearly). One end of the sampling tube 34 is connected to the fasten seat 31 in such a way that the opening 381 is placed in communication with the bore 314 of the fastening seat 31. The sampling tube 34 may be perpendicular to the bottom surface 315 of the recess 313. The sampling tube 34 may be formed integrally with the fastening seat 31. Alternatively, the sampling tube 34 is connected to the bore 314 with suitable method, such as screwing.

A method for assembly of the gas collecting structure 30, in accordance with some embodiments, is described below.

FIG. 6 shows a cross-sectional view of the gas collecting structure 30 as connecting to the exhausting conduit 65a and the gas sensor 40a, in accordance with some embodiments. In some embodiments, the gas collecting structure 30 is connected to the exhausting conduit 65a. The exhausting conduit 65a extends on a flowing axis FA, along which the exhaust flow F from the processing chamber 510 flows.

In cases where the exhausting conduit 65a has a circular cross-section, the flowing axis FA is located on a center of the circular cross-section. A through hole 68 is formed on a side wall of the exhausting conduit 65a, and a passage axis PA passes through a center of the through hole 68. The passage axis PA may be substantially perpendicular to the flowing axis FA. The through hole 68 may be formed in a circular shape with a diameter that is slightly greater than an outer diameter of the encaging member 32.

In assembly of the gas collecting structure 30, the sampling tube 34 is affixed to the fasten seat 31 in advance. Afterwards, the sampling tube 34 is inserted into the exhausting conduit 65a inward from an outer wall 651 to an inner wall 652 via the through hole 68, and the front surface 311 of the fasten seat 31 is abutted against an outside wall 651 of the exhausting conduit 65a.

After the sampling tube 34 is inserted into the exhausting conduit 65a, the engaging member 32 and the shelter member 33 are moved into the exhausting conduit 65a via an open end 650 of the exhausting conduit 65a (the flow-control member 73a is unloaded from the opening end 650 during the assembly of the gas collecting structure 30). Afterwards, the engaging member 32 is inserted into the recess 313 of the fasten seat 31 outward from the inner wall 652 to the outer wall 651 via the through hole 68.

In some embodiments, during the insertion of the engaging member 32 into the recess 313, the passage 320 of the engaging member 32 and the passage 350 of the connecting portion 35 align with the sampling tube 34 to allow the sampling tube 34 to pass through the passage 320 and the passage 350. After the engaging member 32 is inserted into the recess 313, the engaging member 32 is affixed to the fasten seat 31 via a threaded engagement, and the assembly of the gas collecting structure 30 is completed.

Still referring FIG. 6, in some embodiments, the center C1 of the sampling tube 34 and the center C2 of the cross-section of the extension portion 36 may align with the passage axis PA. In addition, the opening 372 of the outer channel 37 and the opening 382 of the inner channel 38 are arranged on the passage axis PA. Moreover, the extension direction E of the sampling tube 34 and the extension portion 36 may be substantially parallel to the passage axis PA and be substantially perpendicular to the flowing axis FA.

In some embodiments, as seen from an upstream side of the sampling tube 34 that is located in exhausting conduit 65a, the sampling tube 34 is covered by the shelter member 33, but the sampling tube 34 is exposed by the shelter member 33 as seen from a downstream side of the sampling tube 34 that is away from the processing chamber 510.

Specifically, when the gas collecting structure 30 is affixed to the exhausting conduit 65a, the sampling tube 34 has a segment 341. The extension portion 36 of the shelter member 33 is located at the upstream side of the segment 341 that is close to the processing chamber 510, and the long cut 365 of the shelter member 33 is located at the downstream side of the segment 341. That is, the extension portion 36, the segment 341 and the long cut 365 are arranged along an alignment axis AA, which is substantially parallel to the flowing axis FA, in order. Therefore, contamination particles from the upstream side can be blocked by the shelter member 33, and the sampling tube 34 is protected from being contaminated.

In some embodiments, the segment 341 of the sampling tube 34 is positioned in the outer channel 37 of the shelter member 33 and is spaced from the opening 372 and the long cut 365 by a distance.

For example, as shown in FIG. 6, in the extension direction E of the sampling tube 34, the segment 341 of the sampling tube 34 may have a length L1 that is shorter than a length L2 of the extension portion 36 of the shelter member 33. Namely, the opening 372 of the outer channel 37 is located farther away from the through hole 68 than the opening 382 of the inner channel 38. In the following description, the opening 372 of the outer channel 37 is referred to as "outer opening", and the opening 382 of the inner channel 38 is referred to as "inner opening", for the purpose of brevity. In one certain embodiment, the length L2 is less than a half of a width of the exhausting conduit 65a, such that the exhaust flow F can smoothly pass through the shelter member 33 with no or less turbulence flow produced.

However, it should be appreciated that many variations and modifications can be made to embodiments of the disclosure. The length L2 can be greater than a half of a width of the exhausting conduit 65a. The end of the extension portion 36 of the shelter member 33 can be modified according to the position where the most of the exhausting conduit 65a may pass in the exhausting conduit 65a. For example, the end of the extension portion 36 is aligned with the center of the exhausting conduit 65a to collect the exhaust flow F passes through the center of the exhausting conduit 65a.

In addition, as shown in FIG. 4, the center C1 of the sampling tube 34 aligns with the center C2 of the extension portion 36 and is spaced from the connecting line CL of the lower edges 363 and 364 by a distance D. The distance D is greater than a half of an outer diameter of the sampling tube 34, and as such the connecting line CL does not pass through the sampling tube 34. However, it should be appreciated that many variations and modifications can be made to embodiments of the disclosure. In some other embodiments, the distance D is equal to or slightly less than a half of an outer diameter of the sampling tube 34, and the connecting line CL passes through the sampling tube 34.

The advantages of the gas collecting structure 30 due to the above-mentioned structural features will be described in more details in relation to FIGS. 6 and 8.

In some embodiments, after the gas collecting structure 30 is mounted on the exhausting conduit 65a, the gas sensor 40a is connected to the fasten seat 31 of the gas collecting structure 30 via a gas line 45. In addition, the flow-control member 73a is affixed to the opening end 650 of the exhausting conduit 65a and electrically connected to the gas sensor 40a.

In accordance with some embodiments, the structural feature of flow-control member 73a is described below. In some embodiments, the flow-control member 73a is a throttle valve and includes a housing 732, a valve body 734 and a controller 736. The housing 732 is connected to the exhausting conduit 65a via a suitable method, such as screwing or welding. The valve body 734 is positioned in the housing 732 in a rotatable manner. The controller 736 is electrically connected to the gas sensor 40a to receive the data from the gas sensor 40a. The controller 736 may analyze data the from the gas sensor 40a and adjust a rotation angle of the valve body 734 in the housing 732. By adjusting the angle of the valve body 734 of the flow-control member 73a through proper means such as a motor, the amount of the exhaust flow from the corresponding wafer processing apparatuses 50a are regulated.

Figure 7:
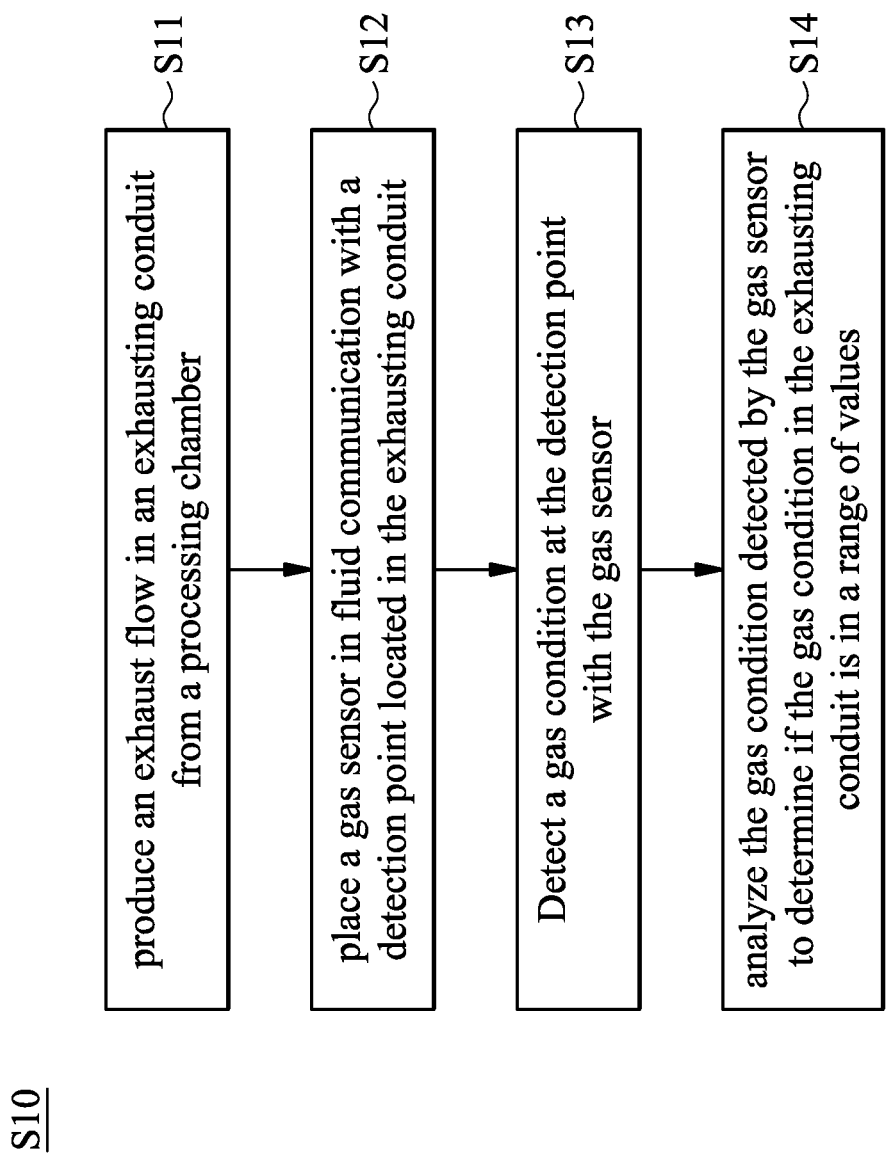
FIG. 7 shows a flow chart of a method for monitoring gas condition in an exhausting conduit, in accordance with some embodiments.

FIG. 7 shows a flow chart of a method S10 for monitoring gas in a wafer processing system, in accordance with some embodiments. For illustration, the flow chart of FIG. 7 will be described along with the figures shown in FIGS. 1, 4, 6 and 8. Some of the stages described can be replaced or eliminated for different embodiments.

The method S10 includes operation S11, in which a exhaust flow F in an exhausting conduit, such as exhausting conduit 65a, is actuated. In some embodiments, as shown in FIG. 1, the exhaust flow F is exhausted from the wafer processing apparatus 50a and flows to the gas handling apparatus 80 via the exhausting conduits 65a, the domain conduit 63 and the main conduit 61. The exhaust flow F may be actuated while one or more wafers are processed in the wafer processing apparatus 50a.

The method S10 also includes operation S12, in which the gas sensor 40a in fluid communication with a detection point DP is disposed in the exhausting conduit 63a via the sampling tube 34. In some embodiments, as shown in FIG. 6, the detection point DP is located at the inner opening 382 of the sampling tube 34. The exhaust flow F at the detection point DP can be guided to the gas sensor 40a via the sampling tube 34.

The method S10 also includes operation S13, in which a gas condition of the exhaust flow F in the exhausting conduit 65a is detected with the gas sensor 40a. The gas sensor 40a may detect exhaust pressure of the exhaust flow F, concentration of particles in the exhaust flow F, temperature of the exhaust flow F or other condition of the exhaust flow F.

In some embodiments, the gas sensor 40a is placed in fluid communication with the exhausting conduit 65a via gas line 45 and the inner channel 38 and detects the gas condition of the exhaust flow F at the detection point DP which is located in the vicinity of the inner opening 382 of the inner channel 38. Due to the fact that the detection point DP is located closer to the middle of the exhausting conduit 65a (i.e., the flowing axis FA) than the through hole 68, as shown in FIG. 6, the gas condition can be more accurately detected as compared with a conventional method in which the gas sensor detects gas in vicinity to the through hole 68.

In some embodiments, the exhaust flow F may contain particles, such as photoresist from the processing chamber 510, and the particles may be accumulated on the gas collecting structure 30. However, because the extension portion 36 is located at an upstream side of the sampling tube 34, the contaminant particles 100 are accumulated on the extension portion 36, as shown in FIG. 8. Therefore, the concern that the inner opening 382 may be blocked by the particles can be eased, and the detection accuracy of the gas condition in the exhausting conduit 65a is improved.

In addition, the arrangements that the sampling tube 34 is spaced from the outer opening 372 and the long cut 365 by a distance also keep the contaminant particles away from the inner opening 382 of the sampling tube 34. Therefore, the issue that the inner opening 382 of the sampling tube 34 is contaminated by particles accumulated on the shelter member 33 when the exhausting conduit 65a is not cleaned for a long time period can be avoided or mitigated.

It should be noted that while a portion of the gas collecting structure 30 is positioned in the exhausting conduit 65a, a disturbance to the exhaust flow F is quite small or negligible. This is because the width of the cross-section of the extension portion 36, as shown in FIG. 4, is gradually increased in a direction along which the exhaust flow F flows, and therefore the exhaust flow F can smoothly pass through the shelter member 33.

Figure 8:
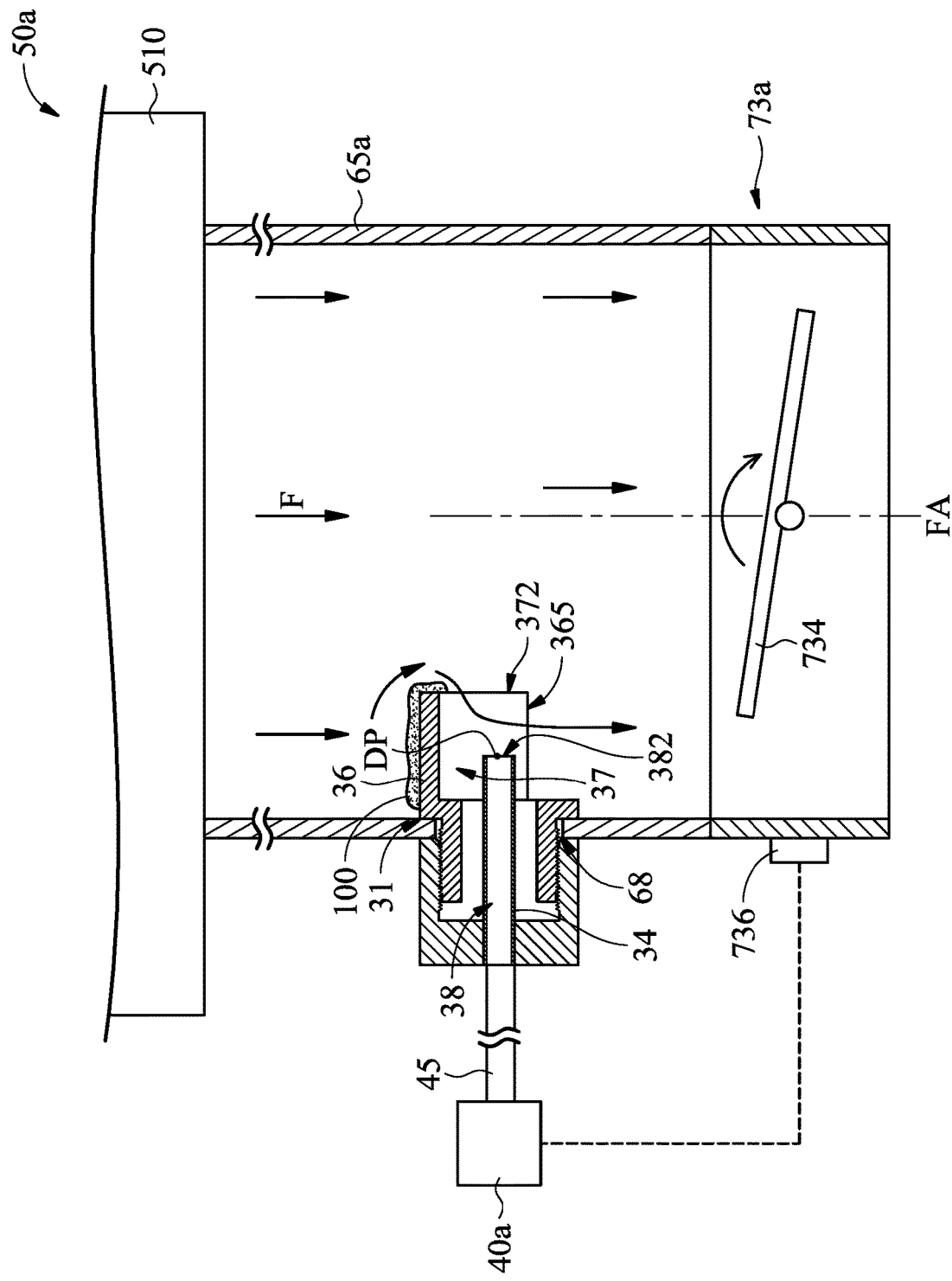
FIG. 8 shows a cross-sectional view of a gas collecting structure with contaminated particle accumulated on an upstream side thereof after a period of use, in accordance with some embodiments.

Additionally, because the exhaust flow F can enter the outer channel 37 via the outer opening 372 and leave the outer channel 37 via the long cut 365 along the direction indicated by the arrow shown in FIG. 8, a real gas condition in the exhausting conduit 65a can be detected by the gas sensor 40a event thought the sampling tube 34 is received in the outer channel 37.

The method S10 also includes operation S14, in which the gas condition detected by the gas sensor 40a is analyzed to determine if the gas condition in the exhausting conduit is in a predetermined value of range. In some embodiments, the data associated with the gas condition is produced by the gas sensor 40a and is sent to the controller 736 of the flow-control members 73a. The controller 736 analyzes the received data to determine if the data associated with the gas condition is in a range of values. The range of values may indicate that normal conditions in the exhausting conduit 65a consistently occur. For example, when the exhausting pressure in the exhausting conduit 65a is within a range of values, the hazardous material for the wafer can be exhausted from the processing chamber 510.

In some embodiments, when the data processed by the controller 736 indicates that the detected gas condition has departed from the range of values, the controller 736 controls the rotation angle of the valve body 734 to adjust the gas condition in the exhausting conduit 65a. For example, when the exhaust pressure in the exhausting conduit 65a is lower than the range of values, the controller 736 adjust the rotation angle of the valve body 734 to increase the exhaust pressure in the exhausting conduit 65a to prevent wafer scrap.

In some embodiments, when the detected exhaust pressure in the exhausting conduit 65a is below the range of values for a predetermined period, and the flow-control member 73a is in a full-open status (in other words, the flow-control member 73a has allowed a maximum amount of flow to pass through), the controller 736 may trigger an alarm. The alarm may indicate a fault (or abnormality) in the exhausting conduit 65a, such as the inner wall of the exhausting conduit 65a is clogged by the photoresist, which may adversely diminish the flow rate of the exhaust flow F in the exhausting conduit 65a and causes wafer scrap in the processing chamber 510.

After the alarm is triggered, the operation of the process being performed by the wafer processing apparatus 50a may be stopped, and an operator of the wafer processing apparatus 50a may be notified to identify and remedy the issue to prevent excessive scrap wafer from being produced in the wafer processing apparatus 50a. For example, the operator of the wafer processing apparatus 50a may perform a maintenance process to clean the exhausting conduit 65a and/or the processing chamber 510. Alternatively, the operator of the wafer processing apparatus 50a may replace the gas collecting structure 30 with another new one.

Embodiments of a method and system for monitoring an exhaust flow in a wafer processing system use a gas collecting structure to allow an exhaust flow to be detected by a gas sensor. Since the gas collecting structure extends inward into an exhausting conduit along which the exhaust flow flows, a gas condition in the exhausting conduit can be monitored more accurately. Therefore, processing parameters of the wafer processing system can be well controlled according to the detected gas condition, and a product yield improvement of wafer can be achieved. In addition, since a sampling tube of the gas collecting structure that communicates between the gas sensor and the exhausting conduit is appropriately protected by a shelter member, false alarm due to clogged particles in an opening of the sampling tube will not happen, and therefore the throughput of the wafer processing system is increased.

In accordance with some embodiments, a wafer processing system is provided. The wafer processing system includes a processing chamber and an exhausting conduit connected to the processing chamber. The wafer processing system further includes a sampling tube. The sampling tube is positioned in the exhausting conduit and extending along an extension direction. The wafer processing system also includes a shelter member. The shelter member positioned at an upstream side of the sampling tube that is close to the processing chamber, and the sampling tube is covered by the shelter member as seen from the upstream side. In addition, the wafer processing system includes a gas sensor. The gas sensor is connected to the sampling tube and configured to monitor gas condition in the exhausting conduit.

In accordance with some embodiments, a wafer processing system is provided. The wafer processing system includes an exhausting conduit configured to guide an exhaust flow. The exhausting conduit has a through hole, and a passage axis passes through the through hole. The wafer processing system further includes a shelter member. The shelter member is positioned in the exhausting conduit and includes an outer channel extends along the passage axis, and the outer channel has an outer opening arranged on the passage axis. The wafer processing system also includes a sampling tube. The sampling tube is positioned in the outer channel and includes an inner channel extends along the passage axis. The sampling tube has an inner opening arranged on the passage axis, and the outer opening is located farther away from the through hole than the inner opening. In addition, the wafer processing system includes a gas sensor. The gas sensor is connected to the sampling tube and configured to monitor gas condition in the exhausting conduit.

In accordance with some embodiments, a method for monitoring gas in a wafer processing system is provided. The method includes producing an exhaust flow in an exhausting conduit from a processing chamber. The method further includes placing a gas sensor in fluid communication with a detection point located in the exhausting conduit via a sampling tube that passes through a through hole formed on the exhausting conduit. The detection point is located away from the through hole. The method also includes detecting a gas condition at the detection point with the gas sensor. The gas sensor is connected to a sampling tube positioned in the exhausting conduit, and the sampling tube is covered by a shelter member positioned at an upstream side of the sampling tube that is close to the processing chamber. In addition, the method also includes analyzing the gas condition detected by the gas sensor to determine if the gas condition in the exhausting conduit is in a range of values.

Although the embodiments and their advantages have been described in detail, it should be understood that various changes, substitutions, and alterations can be made herein without departing from the spirit and scope of the embodiments as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. A wafer processing system, comprising:
   an exhausting conduit configured to guide an exhaust flow, wherein the exhausting conduit has a through hole, and a passage axis passes through the through hole;
   a shelter member positioned in the exhausting conduit, comprising:
      a connecting portion having a plate-shaped body; and
      an extension portion having an arc-shaped body and connected to the connecting portion, wherein the extension portion comprises an outer channel extending along the passage axis, and the outer channel has an outer opening arranged on the passage axis;
   a sampling tube positioned in the outer channel and comprising an inner channel, a first portion, and a second portion, wherein the sampling tube has an inner opening arranged on the passage axis, and the outer opening is located farther away from the through hole than the inner opening, wherein in a bottom view, the first portion of the sampling tube is covered by the shelter member, and the second portion of the sampling tube is exposed from the shelter member; and
   a gas sensor connected to the sampling tube and configured to monitor a gas condition in the exhausting conduit.

2. The wafer processing system as claimed in claim 1, wherein, in a plane that is perpendicular to the passage axis, the outer channel has an arc-shaped cross-section.

3. The wafer processing system as claimed in claim 2, wherein, in the plane that is perpendicular to the passage axis, a connecting line between two lower edges of the arc-shaped cross-section does not pass through the inner channel.

4. The wafer processing system as claimed in claim 2, wherein an arc angle of the arc-shaped cross-section is greater than 180 degrees.

5. The wafer processing system as claimed in claim 1, wherein the shelter member partially surrounds the sampling tube, and a long cut is formed at the shelter member, wherein the long cut extends in an extension direction that is parallel to the passage axis and is communicated with the outer channel.

6. The wafer processing system as claimed in claim 1, wherein the passage axis is perpendicular to a flowing axis along which the exhausting conduit extends.

7. The wafer processing system as claimed in claim 1, further comprising:
   a fastening seat positioned outside the exhausting conduit and having a bore positioned relative to the through hole of the exhausting conduit, wherein the sampling tube passes through the through hole and is connected to the bore; and
   an engaging member passing through the through hole and surrounding the sampling tube, wherein the engaging member is connecting the fastening seat to the shelter member, and the engaging member has external thread.

8. The wafer processing system as claimed in claim 1, further comprising:
a flow-control member configured to adjust the exhaust flow in the exhausting conduit according to data associated with the gas condition detected by the gas sensor, wherein the flow-control member comprises:
a housing;
a valve body positioned in the housing; and
a controller disposed on the exhausting conduit, wherein the flow-control member is connected to a downstream side of the sampling tube.

9. A wafer processing system, comprising:
an exhausting conduit configured to guide an exhaust flow, wherein the exhausting conduit has a through hole, and a passage axis passes through the through hole;
a shelter member positioned in the exhausting conduit, comprising:
a connecting portion having a plate-shaped body; and
an extension portion having an arc-shaped body and connected to the connecting portion, wherein the extension portion comprises an outer channel extending along the passage axis, the outer channel has an outer opening arranged on the passage axis, and the extension portion comprises two leg sections connected each other;
a sampling tube positioned in the outer channel and comprising an inner channel, a first portion, and a second portion, wherein the sampling tube has an inner opening arranged on the passage axis, and the outer opening is located farther away from the through hole than the inner opening, wherein in a bottom view, the first portion of the sampling tube is covered by the shelter member, and the second portion of the sampling tube is exposed from the shelter member; and
a gas sensor connected to the sampling tube and configured to monitor a gas condition in the exhausting conduit.

10. The wafer processing system as claimed in claim 9, wherein the two leg sections respectively have two lower edges, and the connecting line connected between the two lower edges is located away from the sampling tube.

11. The wafer processing system as claimed in claim 9, wherein a cross section of the shelter member has an arc shape, and an arc angle of the cross section of the shelter member is greater than 180 degrees.

12. The wafer processing system as claimed in claim 9, wherein a length of a segment of the sampling tube which is located in the exhausting conduit is less than a length of the shelter member.

13. The wafer processing system as claimed in claim 9, wherein the sampling tube extends along an extension direction, and the extension direction is substantially perpendicular to a flowing axis along which the exhausting conduit extends.

14. The wafer processing system as claimed in claim 9, further comprising:
a fastening seat positioned outside the exhausting conduit and having a bore positioned relative to a through hole formed on the exhausting conduit, wherein the sampling tube passes through the through hole and is connected to the bore; and
an engaging member passing through the through hole of the exhausting conduit, and the shelter member is connected to the fastening seat via the engaging member.

15. The wafer processing system as claimed in claim 9, further comprising:
a flow-control member configured to adjust an exhaust flow in the exhausting conduit according to data associated with the gas condition detected by the gas sensor.

16. The wafer processing system as claimed in claim 9, further comprising:
a wafer stage positioned above the exhausting conduit; and
a dispensing nozzle positioned over the wafer stage for dispensing a photoresist over a semiconductor wafer positioned on the wafer stage.

17. A wafer processing system, comprising:
an exhausting conduit configured to guide an exhaust flow, wherein the exhausting conduit has a through hole, and a passage axis passes through the through hole;
a shelter member positioned in the exhausting conduit, comprising:
a connecting portion having a plate-shaped body; and
an extension portion having an arc-shaped body and connected to the connecting portion, wherein the extension portion comprises an outer channel extending along the passage axis, the outer channel has an outer opening arranged on the passage axis, and a portion of the connecting portion is exposed from the extension portion when viewed along the passage axis;
a sampling tube positioned in the outer channel and comprising an inner channel, a first portion, and a second portion, wherein the sampling tube has an inner opening arranged on the passage axis, and the outer opening is located farther away from the through hole than the inner opening, wherein in a bottom view, the first portion of the sampling tube is covered by the shelter member, and the second portion of the sampling tube is exposed from the shelter member;
a gas sensor connected to the sampling tube and configured to monitor gas condition in the exhausting conduit.

18. The wafer processing system as claimed in claim 17, wherein the outer channel extends along the passage axis, wherein the outer channel has an outer opening arranged on the passage axis.

19. The wafer processing system as claimed in claim 17, further comprising:
a flow-control member configured to adjust the exhaust flow in the exhausting conduit according to data associated with the gas condition detected by the gas sensor, wherein the flow-control member comprises:
a housing connected to the exhausting conduit;
a valve body positioned in the housing; and
a controller disposed on the exhausting conduit and electrically connected to the gas sensor for analyze data the from the gas sensor and adjust a rotation angle of the valve body in the housing.

20. The wafer processing system as claimed in claim 9, further comprising a fasten seat connected to the sampling tube.

* * * * *